(12) United States Patent
Aggarwal (10) Patent No.: US 12,072,332 B2
(45) Date of Patent: Aug. 27, 2024

(54) METHODS AND DEVICE FOR QUANTIFICATION OF ANALYTE

(71) Applicant: VIDCARE INNOVATIONS PVT. LTD., Maharashtra (IN)

(72) Inventor: Rohan Aggarwal, Delhi (IN)

(73) Assignee: VIDCARE INNOVATIONS PVT. LTD., Maharashtra (IN)

( * ) Notice: Subject to any disclaimer, the term of this patent is extended or adjusted under 35 U.S.C. 154(b) by 1300 days.

(21) Appl. No.: 16/488,880

(22) PCT Filed: Feb. 28, 2018

(86) PCT No.: PCT/IN2018/050107
§ 371 (c)(1),
(2) Date: Aug. 26, 2019

(87) PCT Pub. No.: WO2018/158780
PCT Pub. Date: Sep. 7, 2018

(65) Prior Publication Data
US 2020/0182868 A1   Jun. 11, 2020

(30) Foreign Application Priority Data
Feb. 28, 2017   (IN) .............................. 201611029354

(51) Int. Cl.
*G01N 33/543* (2006.01)
*G01N 33/53* (2006.01)

(52) U.S. Cl.
CPC ... *G01N 33/54393* (2013.01); *G01N 33/5308* (2013.01)

(58) Field of Classification Search
None
See application file for complete search history.

(56) References Cited

U.S. PATENT DOCUMENTS

| 5,670,381 | A  | * | 9/1997 | Jou | ...................... | G01N 33/558 |
| | | | | | | 436/538 |
| 2007/0105139 | A1 | * | 5/2007 | Nishigaki | ............ | C12Q 1/6818 |
| | | | | | | 977/924 |
| 2007/0122819 | A1 | * | 5/2007 | Wu | .................. | G01N 33/54373 |
| | | | | | | 435/287.2 |
| 2009/0325276 | A1 | * | 12/2009 | Battrell | .............. | G01N 33/5302 |
| | | | | | | 435/287.2 |
| 2014/0120633 | A1 | * | 5/2014 | Gandini | ............ | B01L 3/502761 |
| | | | | | | 422/69 |

* cited by examiner

*Primary Examiner* — Ann Montgomery
(74) *Attorney, Agent, or Firm* — David S. Bradin; Maynard Nexsen PC (57) ABSTRACT

Methods and device for quantification of an analyte in a sample are provided. An example has the following steps: the sample is introduced into at least one test split channel (306). The test split channel (306) comprises a test reaction portion (306a). The analyte (410) in the sample is to bind to capture reagents (408) provided in the reaction portion. Analyte (410) bound to the capture reagents (408) is contacted with a reactant solution. The reactant solution comprises a plurality of reagent coated microparticles (412) for binding with the analyte (410). Residual reactant solution comprising unbound microparticles is received. The residual reactant solution is analyzed to quantify the analyte.

9 Claims, 8 Drawing Sheets

```
                              ┌── 100
                              ▼
┌─────────────────────────────────────────────────────────────────────┐
│ INTRODUCING THE SAMPLE INTO AT LEAST ONE TEST SPLIT CHANNEL,        │
│ WHEREIN THE TEST SPLIT CHANNEL COMPRISES A TEST REACTION PORTION,   │
│ WHEREIN THE ANALYTE IN THE SAMPLE IS TO BIND TO CAPTURE REAGENTS    │
│ PROVIDED IN THE REACTION PORTION                                    │
│                              102                                    │
└─────────────────────────────────────────────────────────────────────┘
                              │
                              ▼
┌─────────────────────────────────────────────────────────────────────┐
│ CONTACTING THE ANALYTE BOUND TO THE CAPTURE REAGENTS WITH A         │
│ REACTANT SOLUTION, WHEREIN THE REACTANT SOLUTION COMPRISES A        │
│ PLURALITY OF REAGENT COATED MICROPARTICLES FOR BINDING WITH THE     │
│ ANALYTE                                                             │
│                              104                                    │
└─────────────────────────────────────────────────────────────────────┘
                              │
                              ▼
┌─────────────────────────────────────────────────────────────────────┐
│ RECEIVING RESIDUAL REACTANT SOLUTION, WHEREIN THE RESIDUAL          │
│ REACTANT SOLUTION COMPRISES UNBOUND MICROPARTICLES                  │
│                              106                                    │
└─────────────────────────────────────────────────────────────────────┘
                              │
                              ▼
┌─────────────────────────────────────────────────────────────────────┐
│ ANALYZING THE RESIDUAL REACTANT SOLUTION TO QUANTIFY THE ANALYTE    │
│                              108                                    │
└─────────────────────────────────────────────────────────────────────┘
```

```
┌─────────────────────────────────────────────────────┐
│ DETERMINING A DIFFERENCE BETWEEN AN INITIAL NUMBER  │
│ OF REAGENT COATED MICROPARTICLES AND UNBOUND        │
│ MICROPARTICLES                                      │
│ 110                                                 │
└─────────────────────────────────────────────────────┘
                          ↓
┌─────────────────────────────────────────────────────┐
│ CORRELATING THE DIFFERENCE WITH A CONCENTRATION     │
│ OF THE ANALYTE                                      │
│ 112                                                 │
└─────────────────────────────────────────────────────┘
                          ↓
┌─────────────────────────────────────────────────────┐
│ QUANTIFYING THE ANALYTE BASED ON THE CORRELATING    │
│ 114                                                 │
└─────────────────────────────────────────────────────┘
```

```
┌─────────────────────────────────────────────────────┐
│ INTRODUCING THE SAMPLE INTO AT LEAST ONE CONTROL    │
│ SPLIT CHANNEL 116                                   │
└─────────────────────────────────────────────────────┘
                          ↓
┌─────────────────────────────────────────────────────┐
│ WASHING THE SAMPLE FROM THE AT LEAST ONE TEST SPLIT │
│ CHANNEL AND THE AT LEAST ONE CONTROL SPLIT CHANNEL  │
│ 118                                                 │
└─────────────────────────────────────────────────────┘
                          ↓
┌─────────────────────────────────────────────────────┐
│ INTRODUCING THE REACTANT SOLUTION INTO THE AT LEAST │
│ ONE TEST SPLIT CHANNEL AND AT LEAST ONE CONTROL     │
│ SPLIT CHANNEL 120                                   │
└─────────────────────────────────────────────────────┘
                          ↓
┌─────────────────────────────────────────────────────┐
│ RECEIVING BY A TEST DETECTION PORTION OF THE AT     │
│ LEAST ONE TEST SPLIT CHANNEL AND A CONTROL          │
│ DETECTION PORTION OF THE AT LEAST ONE CONTROL SPLIT │
│ CHANNEL RESIDUAL REACTANT SOLUTION 122              │
└─────────────────────────────────────────────────────┘
                          ↓
┌─────────────────────────────────────────────────────┐
│ DETERMINING A DIFFERENCE IN VOLUME OF THE TEST      │
│ DETECTION PORTION AND THE CONTROL DETECTION         │
│ PORTION 124                                         │
└─────────────────────────────────────────────────────┘
                          ↓
┌─────────────────────────────────────────────────────┐
│ CORRELATING THE DIFFERENCE IN VOLUME WITH THE       │
│ DIFFERENCE IN INITIAL NUMBER OF REAGENT COATED      │
│ MICROPARTICLES AND UNBOUND REAGENT COATED           │
│ MICROPARTICLES 126                                  │
└─────────────────────────────────────────────────────┘
```

METHODS AND DEVICE FOR QUANTIFICATION OF ANALYTE

The present application is the U.S. national stage entry, under 35 U.S.C. 371, of PCT Application PCT/IN2018/050107, entitled "Methods And Device For Quantification Of Analyte," filed on Feb. 28, 2018, which in turn claims priority to Indian Application No. 201611029354, filed Feb. 28, 2017, the contents of each of which are hereby incorporated by reference in their entirety, for all purposes.

TECHNICAL FIELD

The present invention relates to quantification of an analyte in a sample, and, in particular, relates to a method and a device for quantification of an analyte in a sample.

BACKGROUND

Generally, tests to diagnose diseases are done in pathology labs. Patient sample, such as sputum, urine, saliva, and the like, are processed by skilled technicians using standard protocols. This is often time-consuming and requires skilled personnel and expensive laboratory equipment. Point of Care (POC) diagnostic methods and devices were developed to reduce time consumed and to, thereby, enable doctors to make clinical decisions. These POC devices include Lateral Flow Assays (LFA) and microfluidic devices. Lab-on-a-chip devices have also been developed to detect, diagnose, and quantify analyte in patient sample.

BRIEF DESCRIPTION OF DRAWINGS

A detailed description is provided with reference to the accompanying figures. In the figures, the left-most digit(s) of a reference number identifies the figure in which the reference number first appears. The same numbers are used throughout the drawings to reference like features and components.

DETAILED DESCRIPTION

The present subject matter relates to a method and a device for quantification of an analyte in a sample.

Diagnostic tests in pathology labs are, typically, time consuming, require skilled technicians, and require a laboratory infrastructure. Point-of-care (POC) devices and methods which provide results in lesser time than laboratory diagnostic tests have been developed. POC devices and method include Lateral Flow Assay (LFA) devices and microfluidic based lab-on-chip based systems.

LFA, though successful, generally lack sensitivity and specificity as provided by laboratory based diagnostic tests. Microfluidic based lab-on-chip based systems provide higher sensitivity and specificity than traditional LFA. Methods have been developed to improve the sensitivity and specificity. However, these methods, typically, require electronic readers which increase cost and complexity of LFA and microfluidic based lab-on-chip based system. Public sector health care providers are generally unable to afford such electronic readers, and therefore, clinical samples are sent to larger laboratories which increase turnaround time (TAT) and diagnosis.

Lab-on-chip systems to detect and measure concentration of analyte in clinical samples that use conventional techniques, such as light reflection, electrical current measurement, and the like, have been developed. While using conventional techniques reduces usage of laboratory equipment, for quantification, handheld or bench-top instruments may be used, in-turn increasing cost.

Recent studies have been aimed at developing assays with increased sensitivity, smaller assay times, and better signal to noise ratio while also maintaining cost. One such assay technique includes using antibody coated microparticles for separation and detection of proteins. As the antibody coated microparticles bind to target proteins, concentration of bound microparticles is directly proportional to concentration of target protein and can be used to quantify the targeted protein. Typically, fluorescent dyes are also coated on the micro-beads to detect bound beads optically. Other methods have also been employed to count bound micro-beads that include use of microscopes, digital or manual cell counters, and the like. These techniques require a laboratory setting and expensive instruments, increasing the complexity of the assay.

In accordance with the present subject matter, the present subject matter provides a method for quantifying an analyte in a sample. The sample is introduced into at least one test split channel. The test split channel comprises a test reaction portion. The analyte in the sample is to bind to capture reagents provided in the reaction portion. Analyte bound to the capture reagents is contacted with a reactant solution. The reactant solution comprises a plurality of reagent coated microparticles for binding with the analyte. Residual reactant solution comprising unbound microparticles is received. The residual reactant solution is analyzed to quantify the analyte.

In one example, the residual reactant solution is analyzed to determine a difference between an initial number of reagent coated microparticles and unbound microparticles.

The difference is correlated with a concentration of the analyte and the analyte is quantified based on the correlating.

In another example, the sample is introduced into at least one control split channel. The reactant solution is introduced into the at least one test split channel and the at least one control split channel. Residual reactant solution is received by a test detection portion of the at least one test split channel and a control detection portion of the at least one control split channel. A difference in volume of the residual reactant solution received by the test detection portion and the control detection portion is determined. The difference in volume is correlated with the difference in initial number of reagent coated microparticles and unbound microparticles. The difference is correlated with a concentration of the analyte and the analyte is quantified based on the correlating.

The present subject matter also provides a microfluidic device for quantification of the analyte in the sample. The microfluidic device comprises a first channel and a microfluidic splitter. A first end of the microchannel splitter is coupled to the first channel and a second end of the microchannel splitter is coupled to a plurality of split channels. The microchannel splitter is to distribute the reactant solution into each of the plurality of split channels. The plurality of split channels comprises the test split channel to receive a first quantity of the reactant solution. The test split channel comprises a test reaction portion. The test reaction portion is to bind the plurality of microparticles and decrease the first quantity of the reactant solution in the presence of the analyte. The test detection portion is to receive a reduced quantity of the reactant solution. The decrease in first quantity is used to quantify concentration of the analyte.

The present subject matter provides a method and device for conducting portable assays that does not use peripheral instrument, such as electronic readers, to assist in its functioning. Further, the present subject provides quantitative results. As the method and device are based on microfluidic devices, the device may be pocket sized. By using the method and device of the present subject matter, analyte can be quantified in a shorted time compared to convention laboratory diagnostic techniques. Further, the method and device do not require any laboratory infrastructure and can be used in resource limited settings, such as rural areas and at home. Further, as the method is simple and the device is easy to use, it can be performed and used by a non-skilled person as well.

The above-mentioned implementations are further described herein with reference to the accompanying figures. It should be noted that the description and figures relate to exemplary implementations, and should not be construed as a limitation to the present subject matter. It is also to be understood that various arrangements may be devised that, although not explicitly described or shown herein, embody the principles of the present subject matter. Moreover, all statements herein reciting principles, aspects, and examples of the present subject matter, as well as specific examples, are intended to encompass equivalents thereof.

Figure 1A:
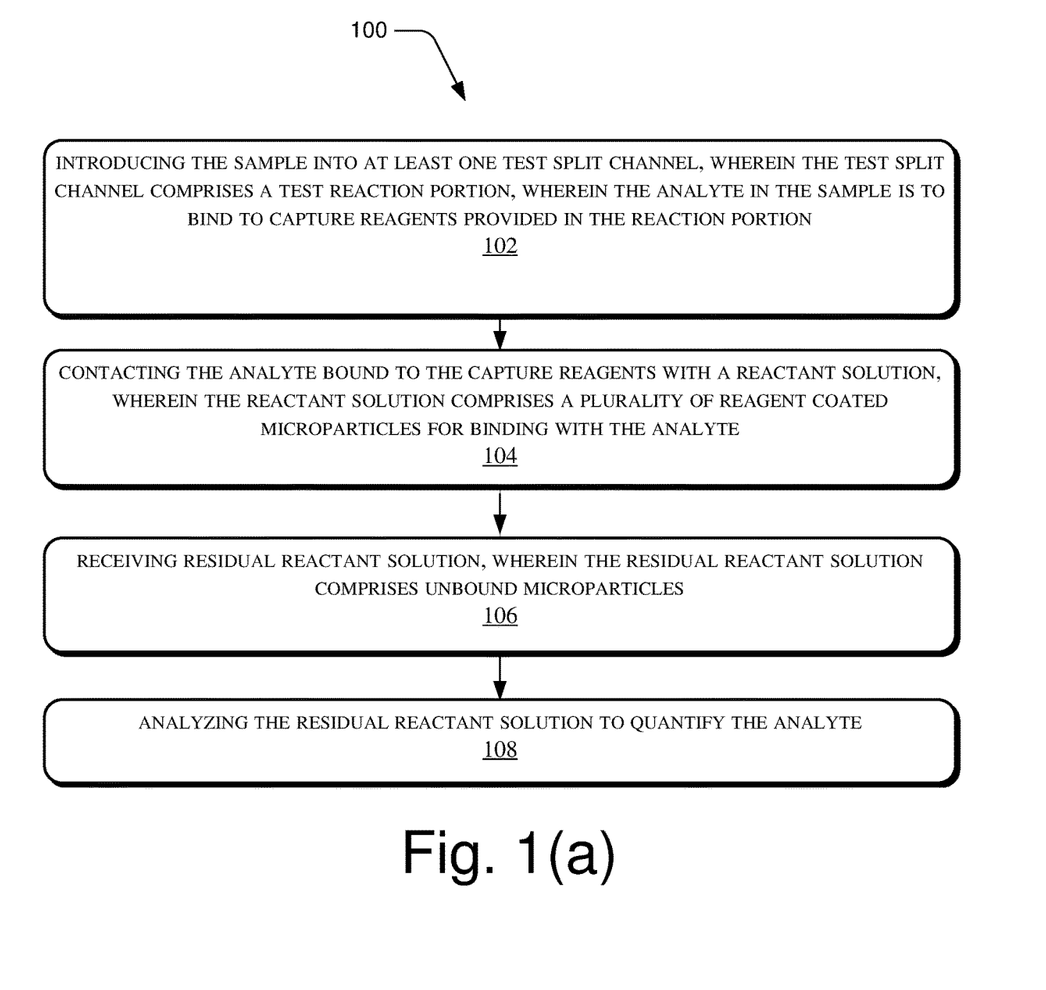
FIG. 1a illustrates a method for quantifying an analyte in a sample, in accordance with an implementation of the present subject matter.

FIG. 1 depicts a method 100 for quantifying an analyte in a sample, in accordance with an implementation of the present subject matter. The analyte may be one of an antigen and an antibody. The analyte is selected from the group consisting of protein, protein fragments, cells, nucleic acids, microbicidal agents, and combinations, thereof. At block 102, the sample is introduced into at least one test split channel. The test split channel will be explained later with reference to FIG. 3. In an example, the sample is introduced at an inlet port of a first channel and subsequently introduced into the test split channel. The test split channel comprises a test reaction portion. Capture reagents are provided in the test reaction portion. For example, the capture reagents may be coated in the test reaction portion. The analyte in the sample is to bind to the capture reagents in the test reaction portion.

At block 104, the analyte bound to the capture reagents is contacted with a reactant solution. The reactant solution comprises a plurality of reagent coated microparticles for binding with the analyte. In an example, contacting comprises hydrating the plurality of reagent coated microparticles with a buffer solution. In another example, contacting comprises hydrating the plurality of reagent coated microparticles with the sample where the plurality of reagent coated microparticles is stored in the reaction portion. The reagent may be an antigen or antibody complementary to the analyte. Contacting the reactant solution with the analyte causes the plurality of reagent coated microparticles to bind to the analyte if the reagent is complementary to the analyte. The reagent is selected from the group consisting of protein, protein fragments, cells, nucleic acids, microbicidal agents, and combinations, thereof, complementary to the analyte being tested.

At block 106, residual reactant solution comprising unbound microparticles are received. In an example, the residual reactant solution is received by a test detection portion. In another example, the residual reactant solution is received into a separate device, for example, a manual counter, a slide, a Neubauer chamber and the like.

Figure 1B:
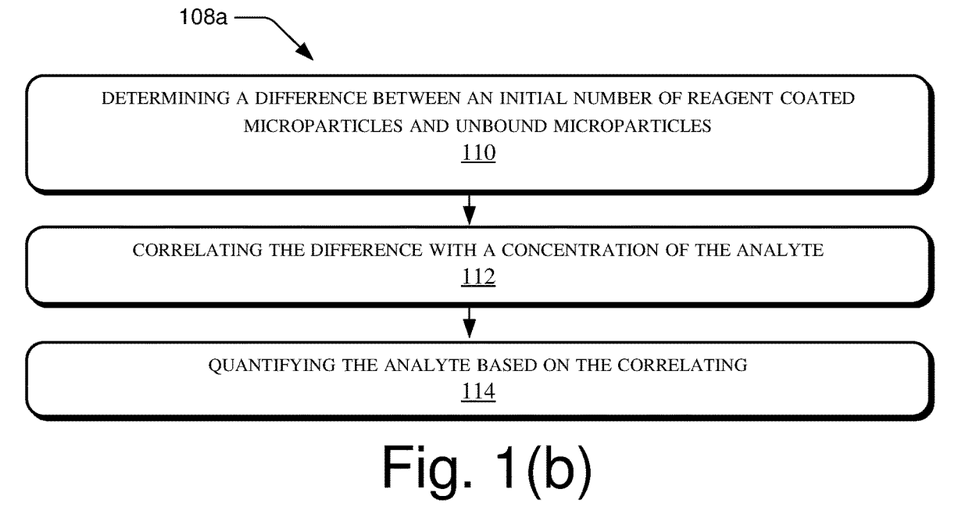
FIG. 1b illustrates a method for analyzing a residual reactant solution, in accordance with an implementation of the present subject matter.

At block 108, the residual reactant solution is analyzed to quantify the analyte. FIG. 1(b) depicts a method 108a for analyzing the residual reactant solution, in accordance with an implementation of the present subject matter. At step 110, a difference between an initial number of reagent coated microparticles and the unbound microparticles is determined. At step 112, the difference is correlated with a concentration of the analyte. At step 114, the analyte is quantified based on the correlating.

Figure 1C:
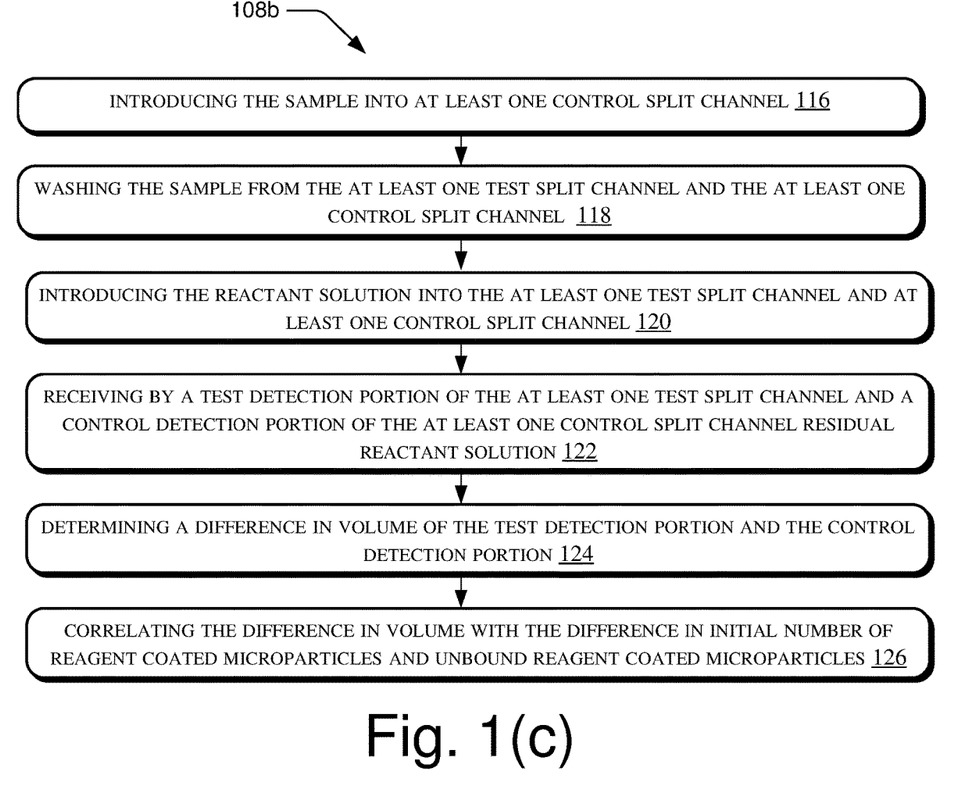
FIG. 1c illustrates another method for analyzing the residual reactant solution, in accordance with an implementation of the present subject matter.

FIG. 1(c) depicts another method 108b for analyzing the residual reactant solution. At block 116, the sample is introduced into at least one control split channel. The sample may be introduced at an inlet port of a first channel. In said example, the sample is then distributed between the at least one test split channel and the at least one split channel from the first channel. In one example, a micropump is used to introduce the sample at the inlet port. In another example, the sample may be introduced using a microinjector and the like. In an example, the sample may be clinical samples, such as sputum, urine, and the like, which may be processed as will be understood. In an example, the sample is diluted and processed prior to introduction at the inlet port. In said example, process sample volume introduced into the inlet port may vary from 1 µL-200 µL. In another example, the sample is introduced at the inlet port without processing or dilution. In said example, the sample volume may vary depending on type of sample used. In one example, flow rate of the sample is between 1 µL/min-200 µL/min. In one example, flow rate of the reactant solution is between 1 µL/min-200 µL/min. However, as will be understood other sample volumes and flow rates may also be used.

In an example, the control split channel also comprises a control reaction portion. In said example, to prevent binding of the analyte in the control reaction portion capture reagents may not be provided in the control reaction portion. In another example, the capture reagents in the control reaction portion may be blocked with analyte analogues. In another example, the analyte is allowed to bind to the plurality of capture reagents in the control reaction portion and bound analyte is subsequently blocked to prevent binding of the plurality of microparticles as will be explained later.

At step 118, the sample is washed from the at least one test split channel and the at least one control split channel. In an example, the washing is performed using a wash buffer. In an example, the washing is performed using different buffers for the at least one test split channel and the at least one control split channel. For example, a blocking buffer may be used to wash the control split channel to block the analyte bound in the control reaction portion.

Subsequent to washing, at step 120, the reactant solution is introduced into the at least one test split channel and the at least one control split channel. The plurality of reagent coated microparticles is to bind to the analyte in the test reaction portion. In an example, the reactant solution is introduced at the inlet port of the first channel and distributed between the at least one test split channel and at least one control split channel. In an example, the plurality of microparticles may be stored upstream of the inlet port in a dehydrated manner. In said example, the plurality of microparticles may be hydrated with a buffer solution to form the reactant solution. In another example, the plurality of microparticles may be stored downstream to the inlet port in a dehydrated manner and may be hydrated due to passage of the sample.

At step 122, a test detection portion of the at least one test split channel and a control detection portion of the at least one control split channel receives residual reactant solution from the at least one test split channel and at least one control split channel. The residual reactant solution comprises unbound microparticles. In one example, the at least one test split channel and at least one control split channel may be washed with a buffer. In said example, the residual reactant solution comprises unbound microparticles and the buffer.

As the plurality of reagent coated microparticles do not bind in the control reaction portion, the residual reactant solution received by the control detection portion is substantially same as volume of the reactant solution introduced. However, as the plurality of microparticles bind to the analyte in the test reaction portion, volume of residual reactant solution received by the test detection portion is reduced. For example, if initial volume of reactant solution introduced into each of the at least one test split channel and at least one control split channel is $V_o$, the residual reactant solution received by control detection portion will be substantially equal to $V_o$ and volume of the residual reactant solution received by the test detection portion $V_1$ will be less than $V_o$ due to binding of the plurality of microparticles in the test reaction portion. At step 124, the difference in volume of the test detection portion and the control detection portion is determined.

The difference in volume is directly proportional to difference in number of microparticles. For example, if initial volume of reactant solution introduced into each of the at least one test split channel and at least one control split comprised $N_o$ number of microparticles, the residual reactant solution received by control detection portion will have microparticles substantially equal to $N_o$ and number of microparticles in the residual reactant solution $N_1$ received by the test detection portion will be less than $N_o$ due to binding of the plurality of microparticles in the test reaction portion. The decrease in volume $V_o$-$V_1$ is representative of the change of number of micro-beads in the test detection channel and control detection channel $N_o$-$N_1$. $N_o$-$N_1$ is further representative of the concentration of the analyte in the test reaction portion.

At step 126, the difference in volume of the test detection portion and the control detection portion is correlated with concentration of the analyte. The difference in volume is correlated with a difference in number of unbound microparticles in the test detection portion and control detection portion. The difference in number of unbound microparticles is correlated with the concentration of the analyte. Based on the correlating the analyte is quantified. Therefore, the method provided by the present subject matter uses volumetric technique to quantify the analyte in the sample.

Figure 2:
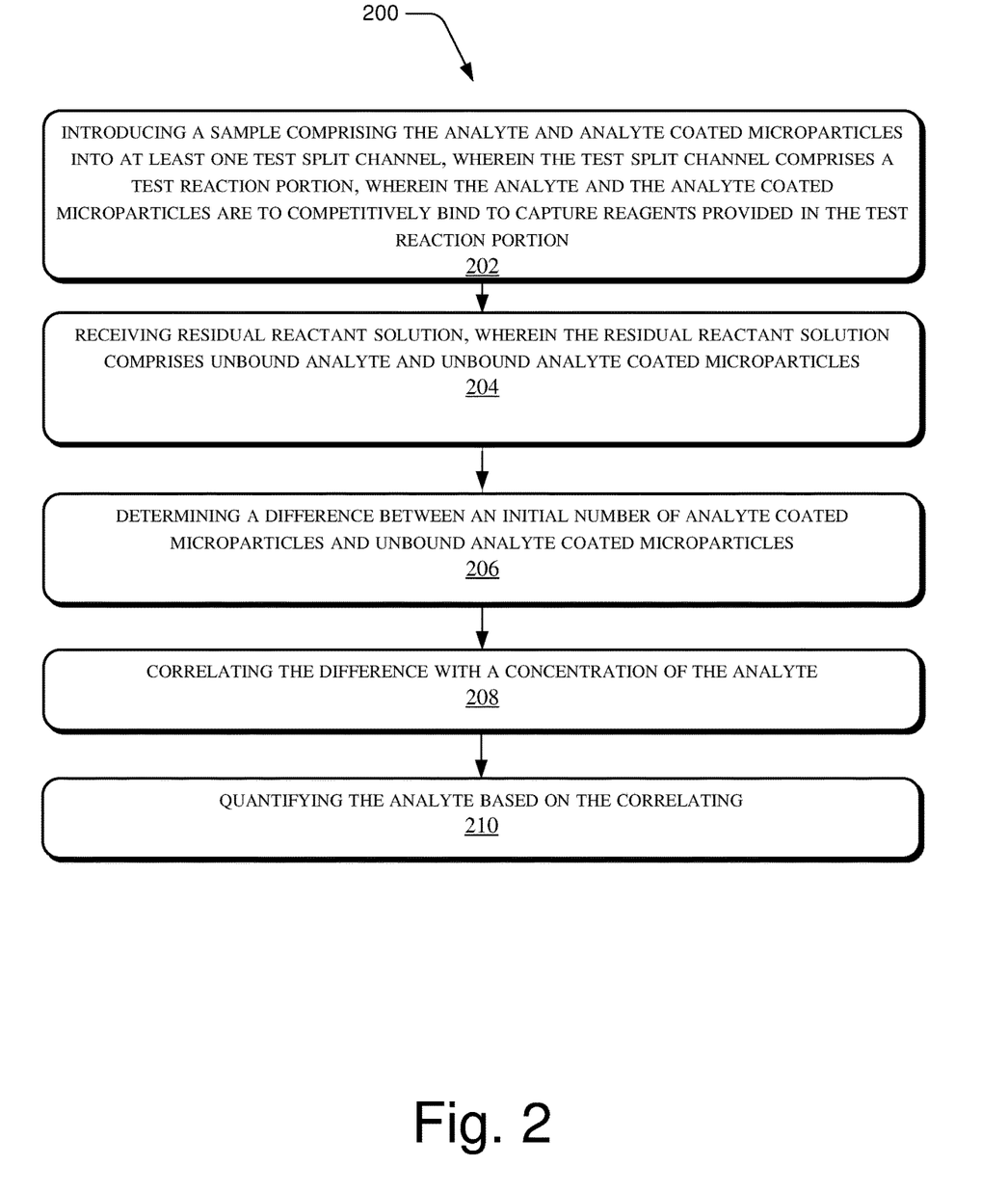
FIG. 2 illustrates yet another method for quantifying an analyte in a sample, in accordance with an implementation of the present subject matter.

FIG. 2 depicts yet another method 200 for quantifying an analyte in a sample, in accordance with an implementation of the present subject matter. At block 202, the sample comprising the analyte and analyte coated microparticles is introduced into at least one test split channel. The analyte and the analyte coated microparticles are to competitively bind to capture reagents provided in the reaction portion.

At block 204, residual reactant solution is received. The residual reactant solution comprises unbound analyte and unbound analyte coated microparticles. For a particular concentration of analyte, the number of unbound analyte coated microparticles in the residual reactant solution remain substantially the same. Therefore, a difference between an initial number of analyte coated microparticles and unbound analyte coated microparticles remains the same for a particular concentration of the analyte.

At block 206, the difference between the initial number of analyte coated microparticles and unbound analyte coated microparticles is determined. At block 208, the difference is correlated with the concentration of the analyte. At block 210, the analyte is quantified based on the correlating.

Figure 3:
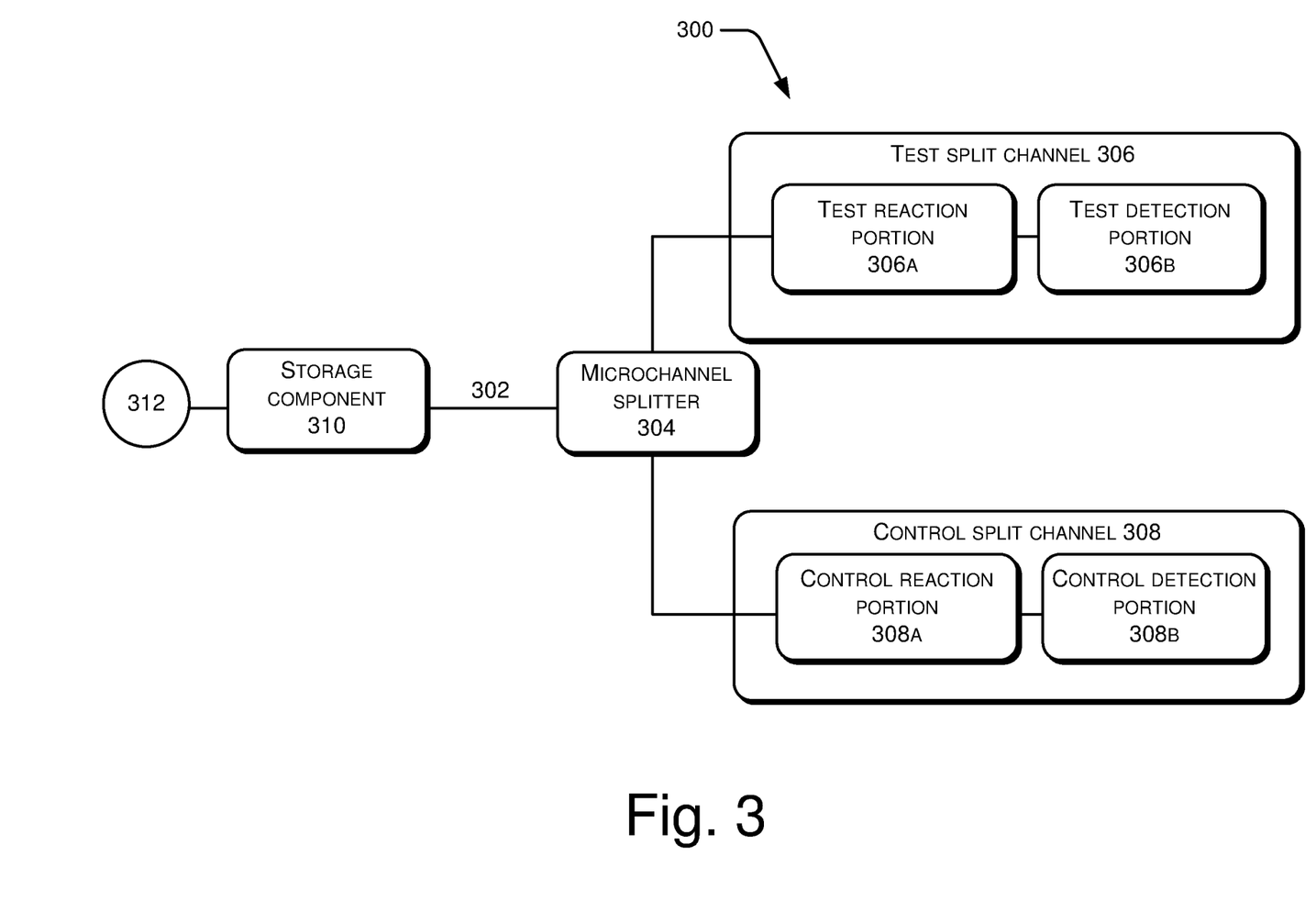
FIG. 3 illustrates a schematic of a device for quantifying the analyte, in accordance with an implementation of the present subject matter.

The present subject matter further provides a microfluidic device for quantification of an analyte. FIG. 3 depicts the microfluidic device 300, in accordance with an implementation of the present subject matter. The microfluidic device 300 comprises a first channel 302 and a microchannel splitter 304. A first end of the microchannel splitter 304 is coupled to the first channel 302 and a second end of the microchannel splitter 304 is coupled to a plurality of split channels.

FIG. 3 depicts two split channels, namely the test split channel 306 and the control split channel 308. However, any number of split channels (test or control) may be provided as will be understood. The microchannel splitter 304 is to distribute a reactant solution into each of the plurality of split channels. In an example, the microchannel splitter 304 may comprise components, such as flow detectors, to ensure equal distribution of the reactant solution into each of the plurality of split channels.

The plurality of split channels comprises a test split channel 306 and a control split channel 308. It is to be understood that multiple test split channels and control split channels may be provided based on factors, such as number of analytes being quantified and the like. The test split channel 306 is to receive a first quantity of the reactant solution from the microchannel splitter 304. The test split channel 306 comprises the test reaction portion 306a. In an example, the test spit channel 306 also comprises the test detection portion 306b. The test reaction portion 306a is to bind to the plurality of reagent coated microparticles and to decrease the first quantity of the reactant solution in the presence of the analyte.

As explained previously, the test reaction portion 306a comprises capture reagents coated therein to capture the analyte, which further binds to the plurality of reagent coated microparticles. Binding of the plurality of reagent coated microparticles decreases the first quantity. The first quantity may be a first volume of the reactant solution or initial number of reagent coated microparticles. The test split channel 306 also comprises a test detection portion 306b to receive a reduced quantity of the reactant solution.

Similar to the test split channel 306, the control split channel 308 also comprises a control reaction portion 308a and a control detection portion 306b. The control detection portion 306b may receive a second quantity of the reactant solution from the microchannel splitter 304 or the control reaction portion 308a. The first quantity and the second quantity are substantially equal. The reduced quantity is correlated to a concentration of the analyte, where the analyte is quantified based on the said correlation.

The test split channel 306 and the control split channel 308 may have different shapes and cross-sections. For example, the test split channel 306 and the control split channel 308 may be serpentine channels, straight channels, circular channels, curved channels, and the like. In one example, the test reaction portion 306a has a smaller cross-sectional diameter that the test detection portion 306b to ensure maximum contact between the analyte and the capture reagents. In another example, different portions of the test split channel 306 and the control split channel 308 may have different cross-section. For example, the test split channel 306 and the control split channel 308 may have a gradient increase or step increase in cross-section.

In an example, characteristic cross-section size of the test split channel 306 and the control split channel 208 may be in range of 20 μm-2000 μm. To enhance specificity and prevent cross-reactivity, the inner surface of the test split channel 306 and the control split channel 308 maybe coated with an inert protein such as Bovine Serum Albumin (BSA). The choice of the blocking agent(s) vary depending on the analyte being quantified.

In an example, the reaction solution comprises the plurality of microparticles suspended in a buffer solution. The plurality of microparticles is coated with the reagent which are complementary to the analyte being quantified. In an example, a size of the plurality of microparticles is in a range of 0.2 μm to 20 μm. In an example, the plurality of microparticles is fabricated from latex, polymers, metals, ceramics, organic compounds, biomolecules, and combinations, thereof.

In one example, the reactant solution comprising the plurality of microparticles is introduced at the microchannel splitter 304. In another example, the plurality of microparticles may be stored in a storage component 310 in a dehydrated state. In one example, the storage component 310 is upstream to the first channel 302 as shown in FIG. 3. However, the storage component 310 may also be provided downstream as will be understood. In one example, the plurality of reagent coated microparticles is stored upstream to the sample inlet. In another example, the plurality of reagent coated microparticles is stored in the test reaction portion 306a. They are desiccated and stored until buffer solution or the sample rehydrates the plurality of reagent coated microparticles.

In an example, the plurality of reagent coated microparticles is stored downstream to the microchannel splitter 304. In said example, the plurality of microparticles may be hydrated by the sample. Buffer solutions for rehydration of the plurality of microparticles are stored upstream to the storage component 310. Buffer solutions may be of two types, namely a reaction buffer and a wash buffer. Reaction buffer is placed such that it is downstream relative to the wash buffer, so that the wash buffer can wash off unbound microparticles into the test detection portion 306b and the control detection portion 308b. A switching element 312 may be used to actuate flow of the buffer solution. The switching element 312 may be non-electrical and helps creates a pressure gradient across the microfluidic device 300. The pressure gradient may be a positive pressure gradient or a negative pressure gradient.

In one example, a length of the test detection portion 306b and the control detection portion 308b is in a range of 1 mm-300 mm. The test detection portion 306b and the control detection portion 306b is one of a straight, serpentine, and curved channel and the like. The test detection portion 306b and the control detection portion 308b comprise graduated markings to determine difference between the second volume and the reduced volume.

In an example, the microfluidic device 300 also comprises an inlet port coupled to the first channel 302 for introduction of the sample comprising the analyte. In another example, the inlet port is provided in the first channel 302. The microfluidic device 300 may also comprise a pump to pump the buffer solution into the first channel 302. The microfluidic device 300 may also comprise an actuator to actuate the pump. The operation of the device is further explained with reference to FIG. 1-3.

Figure 4:
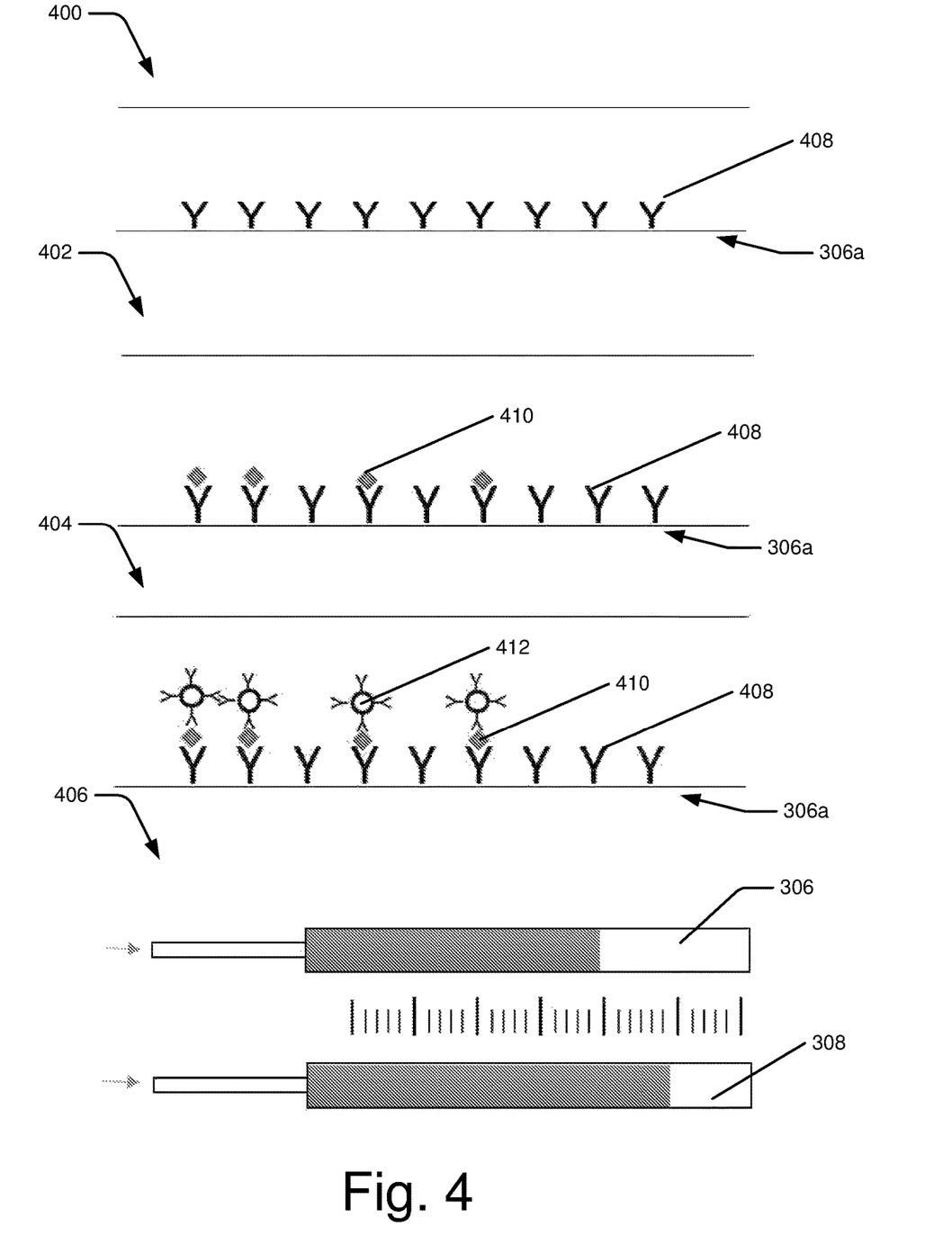
FIG. 4 illustrates pictorial representation of quantification of the analyte, in accordance with an implementation of the present subject matter.

FIG. 4 pictorially depicts an example operation of the microfluidic device 300, in accordance with an implementation of the present subject matter. Step 400 depicts the capture reagents 408 coated on an inner surface of the test reaction portion 306a. Step 400 depicts the capture reagents 408 as antibodies. However, it is to be understood that capture reagents 408 may be antigens as well.

As previously explained, the inlet port may be used to introduce a sample into the microfluidic device 300. In one example, an absorbent pad may be used for introduction of the sample. In the test reaction portion 306a, analyte 410 in the sample binds to the capture reagents 408 as depicted by step 402.

On actuation, buffer solutions start moving through the storage component 310. Reaction buffer rehydrates the desiccated plurality of reagent coated microparticles 412 for binding to the analyte. The reactant solution comprising the plurality of reagent coated microparticles 412 and buffer pass through the microchannel splitter 304 and are distributed between the test split channel 306 and the control split channel 308.

In the test split channel 306, the plurality of microparticles binds to the analyte as shown in step 404. However, as the control split channel 308 do not allow for binding of the analyte, the plurality of reagent coated microparticles pass through the control reaction portion 308a without being bound into the control detection portion 308b. Both the test detection portion 306a and control detection portion 308b are washed. Residual reactant solution and unreacted reactant solution from the test reaction portion 306a and control reaction portion 308b are received by the test detection portion 306b and the control detection portion 308b. Step 406 depicts the test detection portion 306b and the control detection portion 308b. The difference in volume between the control detection portion 308b and the test detection portion 308b may be visually determined and correlated with the concentration of analyte in the sample.

The present subject matter will now be illustrated with working examples, which are intended to illustrate the working of disclosure and not intended to be taken restrictively to imply any limitations on the scope of the present disclosure. Unless defined otherwise, all technical and scientific terms used herein have the same meaning as commonly understood to one of ordinary skill in the art to which this disclosure belongs. It is to be understood that this disclosure is not limited to the particular methods and experimental conditions described, as such methods and conditions may vary depending on the process and inputs used as will be easily understood by a person skilled in the art.

EXAMPLES

Example 1: Optimization Studies

In said example, sample refers to human Thyroid Stimulating Hormone (TSH) (1 mg=7 IU) spiked with Phosphate Buffer Saline (PBS) (pH=7.4). In all runs the concentration was kept constant at ~1 mIU/l, unless otherwise specified. Reactant solution includes carboxyl functionalized polystyrene microparticles suspended in PBS, coated with anti-TSH antibody. Washing buffer used was 0.1% Tween-20 in PBS solution. Further, term 'signal' used hereinafter refers to difference in no. of unbound microparticles between control detection portion 208b and test detection portion 208a.

Prior to the assay, the test reaction portion 206a was coated with capture antibody and the plurality of microparticles were prepared by covalent coupling the microparticles with the anti-TSH antibody. Sample was prepared by spiking PBS with appropriate volume of human-TSH (Sigma) stock. A defined volume of this sample was added to inlet port. Flow was maintained using negative pressure applied through a syringe pump (New Era Pump Systems USA, NE-1000). The sample was allowed to pass through the control split channel and the test split channel completely. The reactant solution was added to the microfluidic device 200, and allowed to pass through it at a controlled flow rate. In the next step, washing buffer (200-300 µL) was passed through the microfluidic device 200. The plurality of microparticles from the control detection portion and the test detection portion were collected in a 1.5 ml micro-centrifuge tube to correlate the number of unbound beads with concentration of analyte.

Example 1.1: Optimization of Sample Flow Rate

Optimization of flow rate for sample was conducted in this example. The following parameters were maintained constantly: sample volume: 50 µl; sample concentration: 1 mIU/l; reaction solution flow rate: 75 µl/min; initial number of microparticles introduced into the microfluidic device 200: $13.87 \times 10^7$. The flow rate range was tested. 25 µl/min was set as lower limit since it keeps the assay step within practical limit of 8-10 minutes. 75 µl/min and 150 µl/min flow rate values also evaluated. Duplicate results were evaluated.

Figure 5:
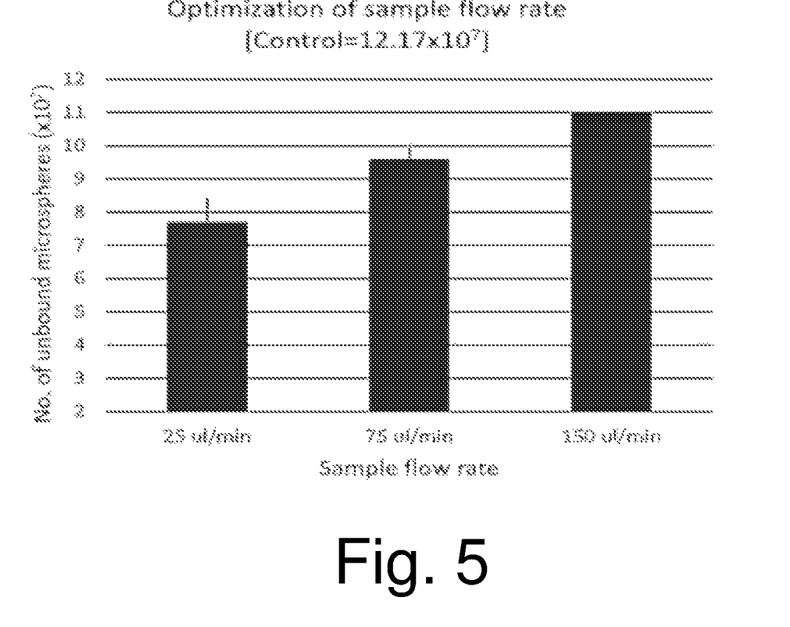
FIG. 5 illustrates result of optimization of sample flow rate, in accordance with an implementation of the present subject matter.

Based on channel geometry due to machining process and system imperfections the flow rate was found to vary between 21-28 µl/min. Control split channel microchannel result showed the mean no of unbound microparticles as $12.17 \times 10^7$, which was considered as reference for the assay. A general trend of increase in unbound microparticles was observed on every increase of sample flow rate, as shown in FIG. 5, as was expected. An approximate change of 40% was seen when moving from a faster flow rate to a slower one, during the study.

Maximum binding was observed at 25 µl/min=$4.11 \times 10^7$ microparticles. 25 µl/min was concluded to be the best flow rate while keeping the assay within practical/target time limit of 15-20 minutes.

Example 1.2: Optimization of Flow Rate for Reactant Solution

Optimization of flow rate for reactant solution was conducted in this example. The following parameters were kept constant: Sample Volume: 50 µl; Sample concentration: 1 mIU/l; Sample flow rate: 75 µl/min; Initial number of microparticles injected: $12.37 \times 10^7$.

Figure 6:
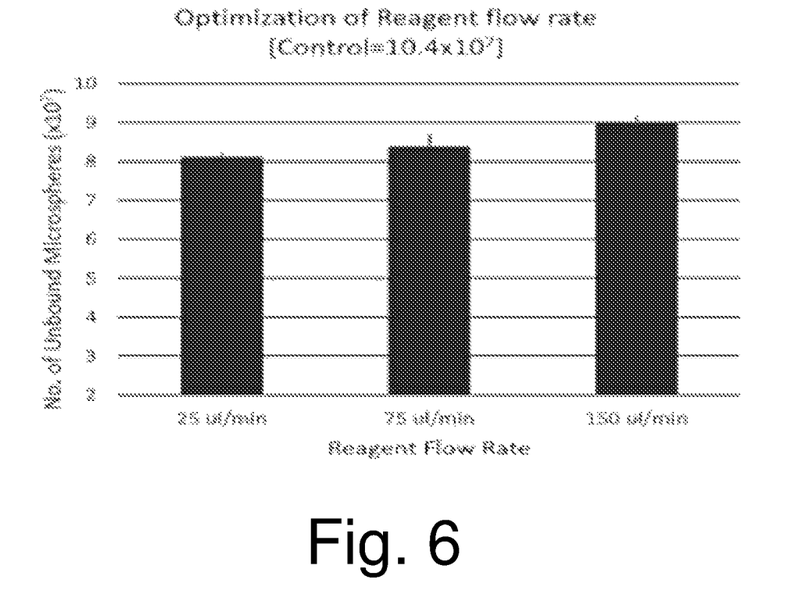
FIG. 6 illustrates result of optimization of reactant solution flow rate, in accordance with an implementation of the present subject matter.

25 µl/min was set as lower limit since it keeps the assay step within practical limit of 8-10 minutes. 75 µl/min and 150 µl/min flow rate values also evaluated. Control microchannel result as shown in FIG. 6 showed the mean number of unbound microparticles across different flow rates as $10.4 \times 10^7$, which was considered as reference for the assay.

A general trend of increase in unbound microparticles was observed on every increase of reagent flow rate, as expected. An approximate change of 30% was seen when moving from 150 µl/min to 75 µl/min, which was reduced to a change of 20% when moving to 25 µl/min. Maximum binding observed at 25 µl/min was $2.2 \times 10^7$ microparticles. 25 µl/min can be considered to be the best flow rate while keeping the assay within practical/target time limit of 15-20 minutes.

Example 1.3: Optimization of Sample Volume

Optimization of sample volume was conducted in this example. The following parameters were kept constant: sample concentration: 1 mIU/l; sample flow rate: 25 µl/min; reactant solution flow rate: 25 µl/min; initial number of microparticles injected: $18.69 \times 10^7$.

10 µl was set as minimum volume used. It was found difficult to manage this small volume at scale of the chamber used, and was, therefore, diluted to 30 µl using PBS. 25 µl was considered as volume for studies as one drop of blood is approximately equal to 25 µl. 50 µl was set as maximum volume since volumes outside of the range are difficult to measure/extract through finger prick.

Figure 7:
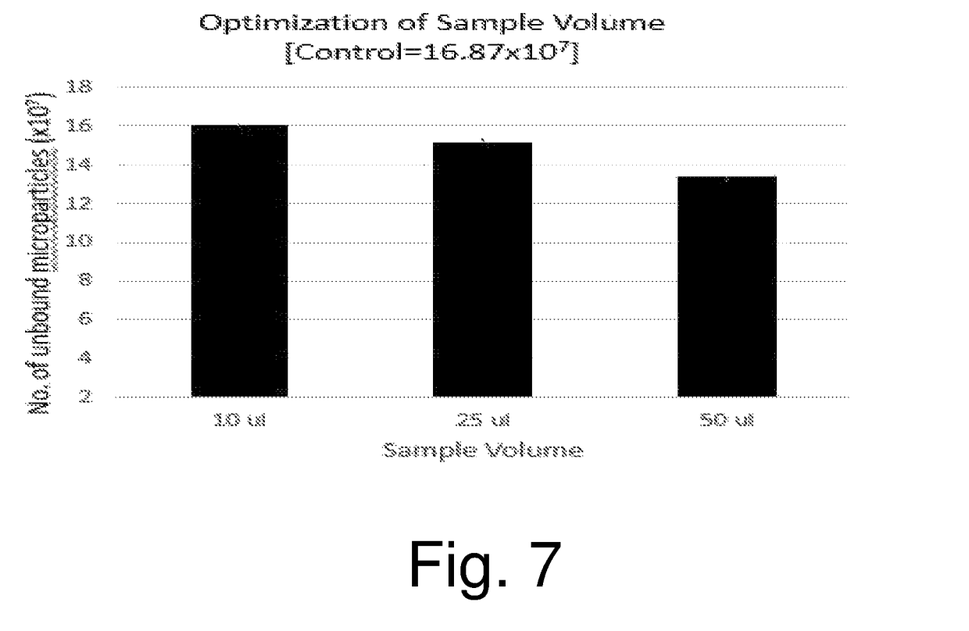
FIG. 7 illustrates result of optimization of sample volume, in accordance with an implementation of the present subject matter.

Control microchannel result as shown in FIG. 7 showed the mean no of unbound microparticles as $16.87 \times 10^7$, which was considered as reference for the assay. A general trend of decrease in unbound microparticles was observed on every increase of sample volume, as expected. The change was proportional to the sample volume used. For example, the change in number of microspheres doubled when volume was increased from 25 µl to 50 µl.

Maximum binding observed at 50 µl volume was $3.47 \times 10^7$ microparticles. 50 µl was considered to be the best volume, since the signal was maximum per unit concentration.

Example 1.4: Standard Curve

Figure 8A:
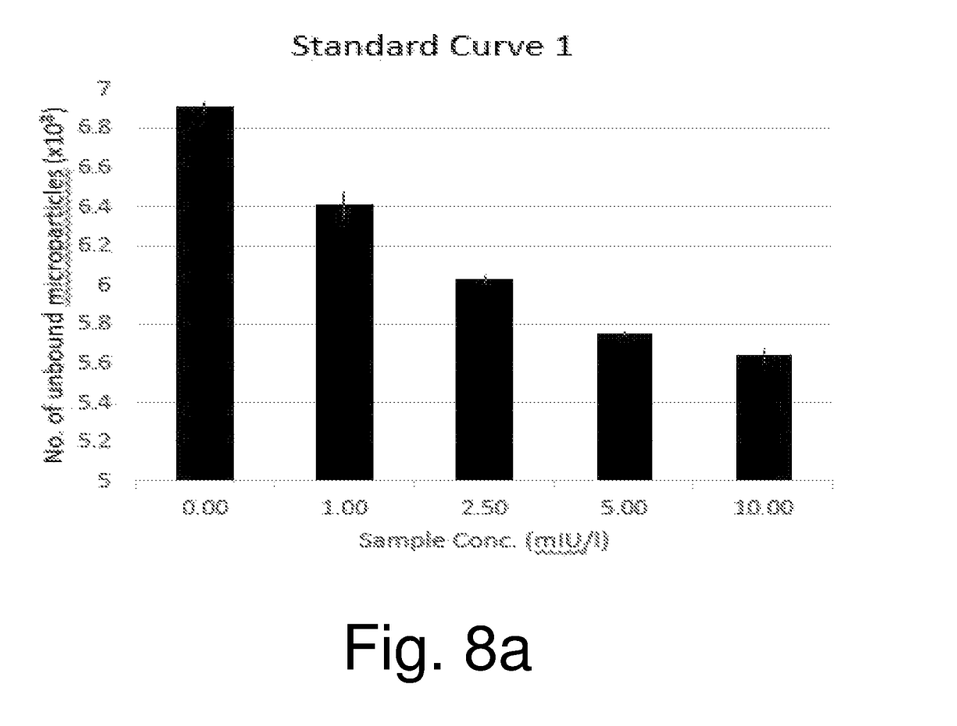
FIG. 8a illustrates a standard curve prepared with respect to number of unbound microparticles, in accordance with an implementation of the present subject matter.
Figure 8B:
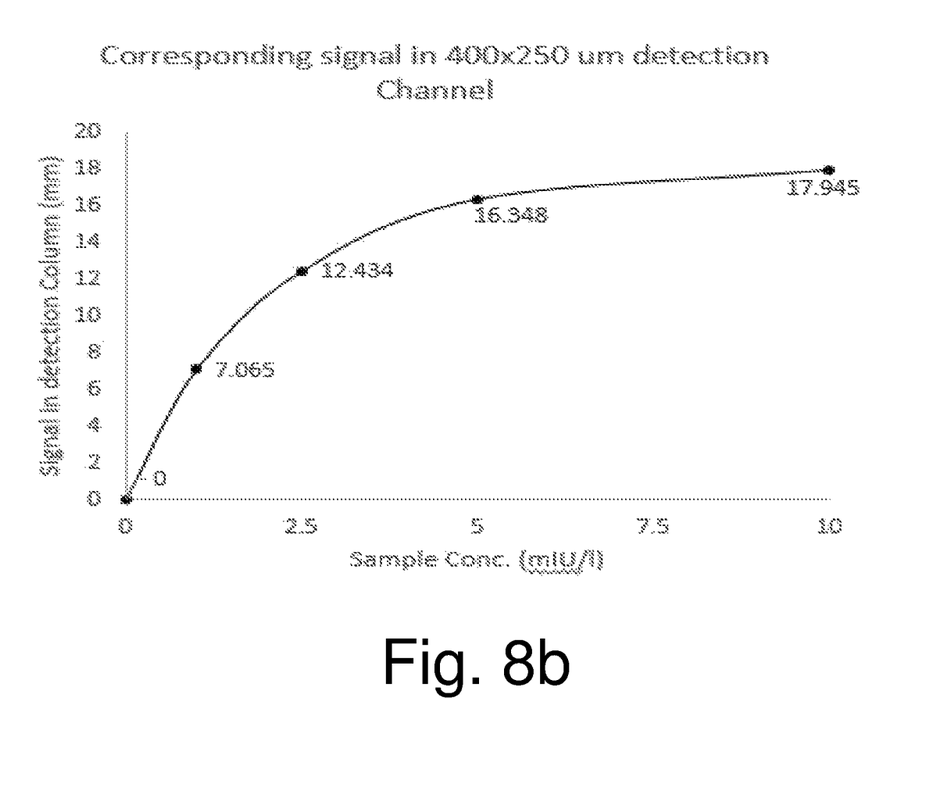
FIG. 8b illustrates a standard curve prepared with respect to signal in detection channel, in accordance with an implementation of the present subject matter.

For preparing the standard curve, the following parameters were kept constant: sample volume: 50 µl; sample flow rate: 25 µl/min; reactant solution flow rate: 25 µl/min; number of microparticles initially injected: $6.5 \times 10^8$; reaction solution concentration and volume~6-6.5%, 160 µl. FIG. 8 show that there is a change of around 7 mm for samples of concentration 1 mIU/l.

A general trend of decrease in unbound microparticles was observed on every increase of sample concentration, as expected. The degree of change though reduces significantly for 1-unit change in concentration soon after.

The reason for the observation is that the microparticles saturate all the binding sites on the designed reaction chamber. As the number of available sites reduce, the binding probability of unbound microparticles also reduce and hence the signal strength is decreased. The degree of change depends on number of available sites after each step. To overcome this limitation, the available surface area in the microfluidic device 200 should be increased.

Various parameters were optimized during the study, namely as follows-reactant solution flow rate—25 µl/min; sample flow rate—25 µl/min; sample volume—50 µl; reactant solution concentration—5-7%, though other concentrations can also be used, since results are comparable. A standard curve was plotted where signal for 1 mIU/l sample was 7 mm, while the signal strength reduced with increase in sample concentration.

The range was kept under practical limits for the targeted assay device. Time limit for both the steps was 8-10 minutes each, while total assay time is under 20 minutes. Additionally, for some cases similar conditions and sample concentration are seen to provide different binding change. This is due to several freeze-thaw cycles of the antigen being used, which affects its activity.

Example 1.5: Correlating Volume of Residual Reactant Solution and Difference in Number of Plurality of Microparticles In said example, correlation of difference between the initial number of reagent coated microparticles and unbound microparticles with difference in volume of the test detection portion and the control detection portion was studied.

As observed from Table 1 in the experiment the difference in the number of microparticles is proportional to change in volume. The results were rounded up to the nearest integer value. Differences appear mostly due to operator error and manufacturing tolerances and defects in different channels. Cross sectional area of channel was ~$3.2 \times 10^{-2}$ mm$^2$

TABLE 1

Correlating volume of residual reactant solution and difference in number of plurality of microparticles

| Number of spheres (approx.) | Linear difference compared to reference sample (in mm) | | |
|---|---|---|---|
| | Trial 1 | Trial 2 | Trial 3 |
| $6.7 \times 10^7$ | 36 | 39 | 38 |
| $13.4 \times 10^7$ | 69 | 72 | 71 |
| $16.7 \times 10^7$ | 86 | 91 | 89 |
| $20.1 \times 10^7$ | 105 | 109 | 108 |
| $33.5 \times 10^7$ | 177 | 185 | 182 |

Although the subject matter has been described in considerable detail with reference to certain examples and implementations thereof, other implementations are possible. As such, the scope of the present subject matter should not be limited to the description of the preferred examples and implementations contained therein.

I claim:

1. A method for quantifying an analyte in a sample comprising:
   introducing a first sample solution comprising the sample into a test split channel that comprises a test reaction portion and a test detection portion,
   wherein the test split channel is adapted to allow solutions introduced into the test split channel to flow from the test reaction portion to the test detection portion, and
   wherein the test reaction portion comprises capture reagents which bind to analyte if present in the sample,
   allowing the sample to flow into the test reaction portion and allowing analyte, if present, to bind to the capture reagents,
   introducing a known initial volume of a reaction solution into the test split channel, which reaction solution comprises a total known number of microparticles that bind to the analyte, if present, which analyte is already bound to the capture reagents,
   allowing the microparticles to bind to the analyte,
   allowing the reaction solution, comprising unbound microparticles, to flow from the test reaction portion into the test detection portion, wherein the amount of the reaction solution that flows into the test detection portion is a residual reaction solution, and
   measuring a volume of the residual reaction solution in the test detection portion,
   wherein the analyte is quantified by comparing the initial volume of the reaction solution
   to the volume of the residual reaction solution, and determining the amount of bound microparticles based on the difference in volume, wherein the difference in volume is due to the number of particles bound to the analyte, subtracting the number of particles bound to the analyte from the initial known number of microparticles in the reaction solution, and quantifying the analyte based on the number of microparticles bound to the analyte.

2. The method of claim 1, further comprising introducing a second sample solution to a control split channel that comprises a control reaction portion and a control detection portion,
   wherein the control split channel is adapted to allow solutions introduced into the control split channel to flow from the control reaction portion to the control detection portion,
   allowing the second sample solution to pass from the control reaction portion to the control detection portion,
   introducing a known volume of a reaction solution into the control split channel, which reaction solution comprises an initial known number of microparticles that bind to the analyte, such that the reaction solution flows through the control reaction portion to the control detection portion, and
   measuring the volume of the reaction solution in the control detection portion, wherein the amount of the reaction solution that flows into the control detection portion is a residual reaction solution,
   wherein the initial number of microparticles in the known volume of the reaction solution should be unchanged when it passes from the control test portion into the control detection portion, since the control test portion does not comprise any capture reagents that would capture the analyte in the control test portion, such that the analyte could react with microparticles in the control test portion, and
   comparing the initial volume of the reaction solution added to the control split channel to the volume of the residual reaction solution in the control detection portion,
   wherein any difference in volume is unrelated to the presence of the analyte in the sample;
   receiving residual reactant solution by a control detection portion of the at least one control split channel;
   determining a difference in volume of the test detection portion and the control detection portion as a substitute for initial number of reagent coated microparticles and unbound microparticles; and correlating the difference in volume with the difference in initial number of reagent coated microparticles and unbound reagent coated microparticles;

correlating the difference with a concentration of the analyte; and quantifying the analyte based on the correlating.

3. The method of claim 2, wherein the first and second sample solutions are simultaneously introduced in an inlet port that splits these sample solutions such that the first sample solution flows through the test split channel, and the second sample solution flows through the control split channel.

4. The method of claim 1, wherein introducing the reaction solution comprises introducing the reaction solution at an inlet port of a first channel.

5. The method of claim 1, wherein the analyte is an antigen or an antibody.

6. The method of claim 1, wherein the capture reagent is an antigen or an antibody.

7. The method of claim 1, wherein the analyte and the capture reagent is selected from the group consisting of protein, protein fragments, cells, nucleic acids, microbicidal agents, and combinations, thereof.

8. The method of claim 1, wherein the introducing a known initial volume of a reaction solution into the test split channel comprises hydrating the plurality of reagent coated microparticles with a buffer solution, wherein the plurality of reagent coated microparticles is stored upstream of the inlet port.

9. The method of claim 1, wherein the introducing a known initial volume of a reaction solution into the test split channel comprises hydrating the plurality of reagent coated microparticles with the sample, wherein the plurality of reagent coated microparticles is stored in test reaction portion, control reaction portion, and a combination thereof.

* * * * *